(12) United States Patent
Pollner et al.

(10) Patent No.: US 7,993,853 B2
(45) Date of Patent: Aug. 9, 2011

(54) METHODS OF NUCLEIC ACID TARGET CAPTURE

(75) Inventors: Reinhold B. Pollner, San Diego, CA (US); Michael M. Becker, San Diego, MA (US); Mehrdad R. Majlessi, Escondido, CA (US)

(73) Assignee: Gen-Probe Incorporated, San Diego, CA (US)

(*) Notice: Subject to any disclaimer, the term of this patent is extended or adjusted under 35 U.S.C. 154(b) by 0 days.

(21) Appl. No.: 11/429,304

(22) Filed: May 5, 2006

(65) Prior Publication Data
US 2006/0252085 A1 Nov. 9, 2006

Related U.S. Application Data

(60) Provisional application No. 60/678,507, filed on May 6, 2005.

(51) Int. Cl.
*G01N 33/53* (2006.01)
*G01N 33/48* (2006.01)
(52) U.S. Cl. .......................... 435/7.2; 436/94
(58) Field of Classification Search .................. None
See application file for complete search history.

(56) References Cited

U.S. PATENT DOCUMENTS

| | | | |
|---|---|---|---|
| 4,358,535 A | 11/1982 | Falkow et al. |
| 4,486,539 A | 12/1984 | Ranki et al. |
| 4,556,643 A | 12/1985 | Paau et al. |
| 4,563,417 A | 1/1986 | Albarella et al. |
| 4,563,419 A | 1/1986 | Ranki et al. |
| 4,581,333 A | 4/1986 | Kourilsky et al. |
| 4,672,040 A | 6/1987 | Josephson |
| 4,716,106 A | 12/1987 | Chiswell |
| 4,731,325 A | 3/1988 | Palva et al. |
| 4,749,647 A | 6/1988 | Thomas et al. |
| 4,751,177 A | 6/1988 | Stabinsky |
| 4,755,458 A | 7/1988 | Rabbani et al. |
| 4,777,129 A | 10/1988 | Dattagupta et al. |
| 4,797,355 A | 1/1989 | Stabinsky |
| 4,818,680 A | 4/1989 | Collins et al. |
| 4,868,105 A | 9/1989 | Urdea et al. |
| 4,894,325 A | 1/1990 | Englehardt et al. |
| 4,895,650 A | 1/1990 | Wang |
| 4,925,785 A | 5/1990 | Wang et al. |
| 5,030,557 A | 7/1991 | Hogan et al. |
| 5,124,246 A | 6/1992 | Urdea et al. |
| 5,200,314 A | 4/1993 | Urdea |
| 5,273,882 A | 12/1993 | Snitman et al. |
| 5,283,174 A | 2/1994 | Arnold et al. |
| 5,288,609 A | 2/1994 | Engelhardt et al. |
| 5,399,491 A | 3/1995 | Kacian et al. |
| 5,547,842 A | 8/1996 | Hogan et al. |
| 5,554,516 A | 9/1996 | Kacian et al. |
| 5,635,352 A | 6/1997 | Urdea et al. |
| 5,645,985 A | 7/1997 | Froehler et al. |
| 5,656,207 A | 8/1997 | Woodhead et al. |
| 5,658,737 A | 8/1997 | Nelson et al. |
| 5,702,896 A | 12/1997 | Collins et al. |
| 5,731,148 A | 3/1998 | Becker et al. |
| 5,731,153 A | 3/1998 | Lucas et al. |
| 5,750,338 A | 5/1998 | Collins et al. |
| 5,989,817 A | 11/1999 | Soderlund et al. |
| 6,013,488 A | 1/2000 | Hayashizaki |
| 6,060,246 A | 5/2000 | Summerton et al. |
| 6,110,678 A * | 8/2000 | Weisburg et al. .................. 435/6 |
| 6,130,038 A | 10/2000 | Becker et al. |
| 6,268,133 B1 * | 7/2001 | Nisson et al. ..................... 435/6 |
| 6,270,962 B1 | 8/2001 | Chamberlin et al. |
| 6,280,952 B1 * | 8/2001 | Weisburg et al. .................. 435/6 |
| 6,310,199 B1 | 10/2001 | Smith et al. |
| 6,428,986 B1 | 8/2002 | Lapidot et al. |
| RE37,891 E | 10/2002 | Collins et al. |
| 6,534,273 B2 | 3/2003 | Weisburg et al. |
| 6,673,940 B1 | 1/2004 | Dervan et al. |
| 2002/0197614 A1 | 12/2002 | Weir et al. |
| 2004/0014644 A1 * | 1/2004 | Efimov et al. ..................... 514/8 |
| 2004/0029111 A1 | 2/2004 | Linnen et al. |
| 2005/0176109 A1 * | 8/2005 | Yumioka et al. ........... 435/70.21 |
| 2008/0319182 A1 | 12/2008 | Birkner et al. |

FOREIGN PATENT DOCUMENTS

| | | |
|---|---|---|
| EP | 0 862 655 B1 | 10/1996 |
| EP | 0808906 B1 | 9/2000 |
| EP | 1 992 693 A1 | 11/2008 |
| WO | 92/15708 A1 | 9/1992 |
| WO | 98/50583 A1 | 11/1998 |
| WO | 00/26412 A1 | 5/2000 |

OTHER PUBLICATIONS

Simard et al Electrophoresis (2001) vol. 22, pp. 2679-2683.*
ccinfoweb.ccohs.ca/help/msds/msdstermse.html, p. 1, Jun. 5, 2008.*
Oxford dictionary of Biochemistry and Molecular Biology (1997, p. 630).* Eli et al (J. Biochem(1999) vol. 125, pp. 790-794).*
Hutton et al (Nucleic Acids Research (1977) vol. 4, pp. 3537-3555).*
http://www.promega.com/biomath/calc11.htm#melt_results, downloaded Aug. 26, 2010.*
Takashi et al., "Sequence-specific DNA purification by triplex affinity capture", Proc. Natl. Acad. Sci., USA, 1992, 89:495-498, National Academy of Sciences, Washington, D.C., USA.
Bostock-Smit et al., "DNA minor groove recognition by bis-benzimidazole analogues of Hoechst 33258: insights into structure-DNA affinity relationships assessed by fluorescence titration measurements", Nucl. Acids Res., 1999, 27(7):1619-1624, Oxford University Press, Great Britain.
Sambrook, et al., "Molecular Cloning, A Laboratory Manual," 2nd ed., 1989, at §§ 1.90-1.91, 7.52, and 9.47-9.51, Cold Spring Harbor Laboratory Press, Cold Spring Harbor, N.Y.
http://ccinfoweb.coohs.ca/help/msds/msdstermse.html "MSDS - An Explanation of Common Terms," Jun. 5, 2008, pp. 2.

(Continued)

*Primary Examiner* — Steven Pohnert
(74) *Attorney, Agent, or Firm* — Jeffrey E. Landes; Christine A. Gritzmacher

(57) ABSTRACT

Methods for efficiently capturing a target nucleic acid from a sample by using a mixture that contains a capture probe specific for the target nucleic acid, the target nucleic acid, and a denaturant chemical, which mixture is incubated at elevated temperature for a short time, are disclosed. Compositions that include a capture probe that specifically binds to a target nucleic acid and a denaturant chemical, which when mixed with the target nucleic acid and incubated at elevated temperature for a short time, promote efficient hybridization of the capture probe and target nucleic acid are disclosed.

20 Claims, 2 Drawing Sheets

OTHER PUBLICATIONS http://www.ccohs.ca/ccohs.html, "CCOHS: About CCOHS," 2005, pp. 3.

Thomas, "Taber's Cyclopedic Medical Dictionary," 1993, pp. 1932-1933, Edition 17, F.A. Davis Company, Philadelphia PA.

Galen and Gambino, "Beyond Normality: The Predictive Value and Efficiency of Medical Diagnoses," 1975, pp. 10-14, Chapt. 2, John Wiley & Sons, New York, NY.

http://www.sigmaaldrich.com/catalog/productdetail, F9037 Formamide for molecular biology, Dec. 18, 2008, pp. 2.

http://www.sigmaaldrich.com/catalog/productdetail, I5513 Imidazole for molecular biology, Dec. 18, 2008, pp. 2.

EP Communication received in corresponding EP App. No. 06 752 336.5, dated Mar. 11, 2010 (4 pp.).

Office Action received in corresponding CA App. No. 2,584,230, dated Nov. 2, 2009 (3 pp.).

Ushijima et al., "Site-specific cleavage of tRNA by imidazole and/or primary amine groups bound at the 5'end oligodeoxyribonucleotides," Biochimica et Biophysica Acta, 1998, pp. 217-223, Elsevier Science B.V., London, UK.

AU 1st Exam Report in corresponding AU App. No. 2006244394, dated Mar. 5, 2010 (3 pp.).

\* cited by examiner

SEQUENCE LISTING

<160> NUMBER OF SEQ ID NOS: 30

<210> SEQ ID NO 1
<211> LENGTH: 152
<212> TYPE: DNA
<213> ORGANISM: Artificial
<220> FEATURE:
<223> OTHER INFORMATION: Strand 1 of synthetic target nucleic acid

<400> SEQUENCE: 1
cctccattcc gttaccaaca gaactggagg cggtacaatg ggtcttgtca tccggtaaag    60
gccaaatata cgagcatcaa catatgtact tatgtatgta tctactatat acatacatat   120
gtacatatat gaataccatc agtctgtgca gt                                 152

<210> SEQ ID NO 2
<211> LENGTH: 121
<212> TYPE: DNA
<213> ORGANISM: Artificial
<220> FEATURE:
<223> OTHER INFORMATION: Strand 2 of synthetic target nucleic acid

<400> SEQUENCE: 2
actgcacaga ctgatggtat tcatatatgt acatatgtat gtatatagta gatacataca     60
taagtacata tgttgatgct cgtatatttg gcctttaccg gatgacaaga cccattgtac    120
c                                                                    121

<210> SEQ ID NO 3
<211> LENGTH: 55
<212> TYPE: DNA
<213> ORGANISM: Artificial
<220> FEATURE:
<223> OTHER INFORMATION: Target capture probe for synthetic target
      nucleic acid
<220> FEATURE:
<221> NAME/KEY: LNA
<222> LOCATION: (1)..(25)

<400> SEQUENCE: 3
cataagtaca tatgttgatg ctcgtaaaaa aaaaaaaaaa aaaaaaaaaa aaaaa          55

<210> SEQ ID NO 4
<211> LENGTH: 30
<212> TYPE: DNA
<213> ORGANISM: Artificial
<220> FEATURE:
<223> OTHER INFORMATION: Detection probe for 5' portion of strand 1 of
      synthetic target nucleic acid

<400> SEQUENCE: 4
cctccagttc tgcttggtaa cggaatggag                                      30

<210> SEQ ID NO 5
<211> LENGTH: 26
<212> TYPE: DNA
<213> ORGANISM: Artificial
<220> FEATURE:
<223> OTHER INFORMATION: Detection probe for 3' portion of strand 1 of
      synthetic target nucleic acid

<400> SEQUENCE: 5
actgcacaga ctgatggtat tcatat                                          26

<210> SEQ ID NO 6
<211> LENGTH: 58
<212> TYPE: DNA
<213> ORGANISM: Artificial
<220> FEATURE:
<223> OTHER INFORMATION: Synthetic capture probe

<400> SEQUENCE: 6
cggtctttct ctcctttcgt ctacgtttaa aaaaaaaaaa aaaaaaaaaa aaaaaaaa       58

<210> SEQ ID NO 7
<211> LENGTH: 62
<212> TYPE: DNA
<213> ORGANISM: Artificial
<220> FEATURE:
<223> OTHER INFORMATION: Synthetic capture probe

<400> SEQUENCE: 7

```
ctactcaggt gttgaggtcg gtctttctct ttaaaaaaaa aaaaaaaaaa aaaaaaaaaa        60
aa                                                                       62

<210> SEQ ID NO 8
<211> LENGTH: 62
<212> TYPE: DNA
<213> ORGANISM: Artificial
<220> FEATURE:
<223> OTHER INFORMATION: Synthetic capture probe

<400> SEQUENCE: 8
cgcgtctagt cctactcagg tgttgaggtt ttaaaaaaaa aaaaaaaaaa aaaaaaaaaa         60
aa                                                                       62

<210> SEQ ID NO 9
<211> LENGTH: 60
<212> TYPE: DNA
<213> ORGANISM: Artificial
<220> FEATURE:
<223> OTHER INFORMATION: Synthetic capture probe

<400> SEQUENCE: 9
tttcacgtgt ctagtcctac tcaggtgttt aaaaaaaaaa aaaaaaaaaa aaaaaaaaaa         60

<210> SEQ ID NO 10
<211> LENGTH: 57
<212> TYPE: DNA
<213> ORGANISM: Artificial
<220> FEATURE:
<223> OTHER INFORMATION: Synthetic capture probe

<400> SEQUENCE: 10
ccttcacagt actggttcac tatctttaaa aaaaaaaaaa aaaaaaaaaa aaaaaaa           57

<210> SEQ ID NO 11
<211> LENGTH: 58
<212> TYPE: DNA
<213> ORGANISM: Artificial
<220> FEATURE:
<223> OTHER INFORMATION: Synthetic capture probe

<400> SEQUENCE: 11
caggttctat ttcactccct taacatttaa aaaaaaaaaa aaaaaaaaaa aaaaaaaa          58

<210> SEQ ID NO 12
<211> LENGTH: 58
<212> TYPE: DNA
<213> ORGANISM: Artificial
<220> FEATURE:
<223> OTHER INFORMATION: Synthetic capture probe

<400> SEQUENCE: 12
ctaagccaac attccaactg tcttctttaa aaaaaaaaaa aaaaaaaaaa aaaaaaaa          58

<210> SEQ ID NO 13
<211> LENGTH: 60
<212> TYPE: DNA
<213> ORGANISM: Artificial
<220> FEATURE:
<223> OTHER INFORMATION: Synthetic capture probe

<400> SEQUENCE: 13
tgcctctaag ccaacattcc aactgtcttt aaaaaaaaaa aaaaaaaaaa aaaaaaaaaa         60

<210> SEQ ID NO 14
```

```
<211> LENGTH: 59
<212> TYPE: DNA
<213> ORGANISM: Artificial
<220> FEATURE:
<223> OTHER INFORMATION: Synthetic capture probe

<400> SEQUENCE: 14
actctttaaa tgattgctgc ctctaattta aaaaaaaaaa aaaaaaaaaa aaaaaaaaa      59

<210> SEQ ID NO 15
<211> LENGTH: 58
<212> TYPE: DNA
<213> ORGANISM: Artificial
<220> FEATURE:
<223> OTHER INFORMATION: Synthetic capture probe

<400> SEQUENCE: 15
taaatgattg ctgcctctaa gccaatttaa aaaaaaaaaa aaaaaaaaaa aaaaaaaa       58

<210> SEQ ID NO 16
<211> LENGTH: 59
<212> TYPE: DNA
<213> ORGANISM: Artificial
<220> FEATURE:
<223> OTHER INFORMATION: Synthetic capture probe

<400> SEQUENCE: 16
ctgttacgca ctctttaaat gattgcttta aaaaaaaaaa aaaaaaaaaa aaaaaaaaa      59

<210> SEQ ID NO 17
<211> LENGTH: 58
<212> TYPE: DNA
<213> ORGANISM: Artificial
<220> FEATURE:
<223> OTHER INFORMATION: Synthetic capture probe

<400> SEQUENCE: 17
ggaatattta acctgctgct ccatctttaa aaaaaaaaaa aaaaaaaaaa aaaaaaaa       58

<210> SEQ ID NO 18
<211> LENGTH: 58
<212> TYPE: DNA
<213> ORGANISM: Artificial
<220> FEATURE:
<223> OTHER INFORMATION: Synthetic capture probe

<400> SEQUENCE: 18
gtgcaggaat atttaacctg ctgcttttaa aaaaaaaaaa aaaaaaaaaa aaaaaaaa       58

<210> SEQ ID NO 19
<211> LENGTH: 58
<212> TYPE: DNA
<213> ORGANISM: Artificial
<220> FEATURE:
<223> OTHER INFORMATION: Synthetic capture probe

<400> SEQUENCE: 19
taggtggtgc aggaatattt aacctttta aaaaaaaaaa aaaaaaaaaa aaaaaaaa        58

<210> SEQ ID NO 20
<211> LENGTH: 58
<212> TYPE: DNA
<213> ORGANISM: Artificial
<220> FEATURE:
<223> OTHER INFORMATION: Synthetic capture probe

<400> SEQUENCE: 20
```
ttttaggtgg tgcaggaata tttaatttaa aaaaaaaaaa aaaaaaaaaa aaaaaaaa    58

<210> SEQ ID NO 21
<211> LENGTH: 57
<212> TYPE: DNA
<213> ORGANISM: Artificial
<220> FEATURE:
<223> OTHER INFORMATION: Synthetic capture probe

<400> SEQUENCE: 21
cgctatagtt ttaggtggtg caggtttaaa aaaaaaaaaa aaaaaaaaaa aaaaaaa    57

<210> SEQ ID NO 22
<211> LENGTH: 58
<212> TYPE: DNA
<213> ORGANISM: Artificial
<220> FEATURE:
<223> OTHER INFORMATION: Synthetic capture probe

<400> SEQUENCE: 22
ttccttcgct atagttttag gtggttttaa aaaaaaaaaa aaaaaaaaaa aaaaaaaa    58

<210> SEQ ID NO 23
<211> LENGTH: 62
<212> TYPE: DNA
<213> ORGANISM: Artificial
<220> FEATURE:
<223> OTHER INFORMATION: Synthetic capture probe

<400> SEQUENCE: 23
ctcttccaat cgtccgcgtg cttaacttat ttaaaaaaaa aaaaaaaaaa aaaaaaaaaa    60
aa    62

<210> SEQ ID NO 24
<211> LENGTH: 57
<212> TYPE: DNA
<213> ORGANISM: Artificial
<220> FEATURE:
<223> OTHER INFORMATION: Synthetic capture probe

<400> SEQUENCE: 24
ctcttccaat cgtccgcgtg cttatttaaa aaaaaaaaaa aaaaaaaaaa aaaaaaa    57

<210> SEQ ID NO 25
<211> LENGTH: 59
<212> TYPE: DNA
<213> ORGANISM: Artificial
<220> FEATURE:
<223> OTHER INFORMATION: Synthetic capture probe

<400> SEQUENCE: 25
catcgctcta cggactcttc caatcgttta aaaaaaaaaa aaaaaaaaaa aaaaaaaaa    59

<210> SEQ ID NO 26
<211> LENGTH: 55
<212> TYPE: DNA
<213> ORGANISM: Artificial
<220> FEATURE:
<223> OTHER INFORMATION: Synthetic capture probe

<400> SEQUENCE: 26
tccccttgat cgcgacctga tctttaaaaa aaaaaaaaaa aaaaaaaaaa aaaaa    55

<210> SEQ ID NO 27
<211> LENGTH: 58
<212> TYPE: DNA

```
<213> ORGANISM: Artificial
<220> FEATURE:
<223> OTHER INFORMATION: Synthetic capture probe

<400> SEQUENCE: 27
ccacaccatc ggttcccccg aagattttaa aaaaaaaaaa aaaaaaaaaa aaaaaaaa            58

<210> SEQ ID NO 28
<211> LENGTH: 57
<212> TYPE: DNA
<213> ORGANISM: Artificial
<220> FEATURE:
<223> OTHER INFORMATION: Synthetic capture probe

<400> SEQUENCE: 28
tatttcttga aagcctcgct ccactttaaa aaaaaaaaaa aaaaaaaaaa aaaaaaa             57

<210> SEQ ID NO 29
<211> LENGTH: 60
<212> TYPE: DNA
<213> ORGANISM: Artificial
<220> FEATURE:
<223> OTHER INFORMATION: Synthetic capture probe

<400> SEQUENCE: 29
catcaacagc tagaaattat ttcttgattt aaaaaaaaaa aaaaaaaaaa aaaaaaaaaa          60

<210> SEQ ID NO 30
<211> LENGTH: 58
<212> TYPE: DNA
<213> ORGANISM: Artificial
<220> FEATURE:
<223> OTHER INFORMATION: Synthetic capture probe

<400> SEQUENCE: 30
taggtggtgc aggaatattt aaccttttaa aaaaaaaaaa aaaaaaaaaa aaaaaaaa            58
```

METHODS OF NUCLEIC ACID TARGET CAPTURE

RELATED APPLICATION

This application claims the benefit under 35 U.S.C. 119(e) of provisional application No. 60/678,507, filed May 6, 2005, which is incorporated by reference herein.

FIELD OF THE INVENTION

The disclosed compositions and methods relate to molecular biology, more particularly to the isolation of nucleic acids from complex mixtures such as samples by using a nucleic acid oligomer specific for the target nucleic acid and a denaturant chemical in the mixture.

BACKGROUND OF THE INVENTION

Many molecular biology procedures such as in vitro amplification and in vitro hybridization of nucleic acids require some preparation or purification of the nucleic acids to make them effective in the subsequent procedure. Methods of nucleic acid purification have been developed that are non-specific and isolate all nucleic acids present in a sample, or isolate different types of nucleic acids based on physical characteristics, or isolate specific nucleic acids from a sample. Many nucleic acid isolation methods involve complicated procedures or use of harsh chemicals, and require a long time to complete. There remains a need for a simple, efficient, and fast method to separate a nucleic acid of interest from other sample components.

SUMMARY OF THE INVENTION

A method is disclosed for isolating a target nucleic acid of interest from a sample, including the steps of mixing a sample containing a target nucleic acid with a capture probe that hybridizes specifically to a target sequence in the target nucleic acid in a solution phase that contains a denaturant chemical and an immobilized probe that binds specifically to the capture probe, to provide a reaction mixture, incubating the reaction mixture at a first temperature in a range of about 60° C. to 95° C. for about 15 minutes or less, incubating the reaction mixture at a second temperature in a range of about 25° C. to 42° C. for about 20 minutes or less, thereby forming a hybridization complex made up of the capture probe hybridized specifically to the target nucleic acid and the immobilized probe bound specifically to the capture probe, in which the hybridization complex is attached to a support via the immobilized probe, and separating the hybridization complex attached to the support from other sample components. In a preferred embodiment, the denaturant chemical is 8 M urea and the first incubation is at about 95° C. for about 10 minutes or less. In a preferred embodiment, the denaturant chemical is imidazole at a concentration from 0.5 M to 4.2 M, and the first incubation is at about 60° C. for about 1 to 15 minutes. Other preferred embodiments, use imidazole at a concentration from 3.0 M to 3.5 M, and incubate at a first temperature of 60° C. for about 1 to 15 minutes. In other preferred embodiments, imidazole at a concentration from 2.0 M to 2.7 M and the first incubation is at about 90° C. to 95° C. for about 3 to 10 minutes. In some preferred embodiments, the denaturant chemical is imidazole at a concentration of 2.7 M, the first incubating temperature is about 75° C. to 95° C. for about 3 to 15 minutes, and the method further includes incubating the reaction mixture at about 60° C. for about 20 minutes between the first and second incubating steps. In a preferred embodiment that uses imidazole at a concentration of 2.7 M, the first incubating temperature is about 95° C. for about 3 to 15 minutes, and the method includes incubating the reaction mixture at about 60° C. for about 20 minutes between the first and second incubating steps. In some embodiments, the target nucleic acid is a completely or partially double-stranded nucleic acid, or a nucleic acid that includes other secondary or tertiary structure. In one embodiment, the capture probe is made up of a target-specific sequence that binds to the target nucleic acid and a tail region that binds to the immobilized probe via a specific binding partner. In a preferred embodiment, the capture probe's tail region binds to the immobilized probe by hybridizing specifically to a complementary sequence of the immobilized probe. Some preferred embodiments also include detecting the target nucleic acid or an in vitro amplification product made from the target nucleic acid after separating the hybridization complex attached to the support from other sample components.

A method is disclosed for isolating a target nucleic acid of interest from a sample that includes the steps of mixing a sample containing a target nucleic acid with a capture probe that hybridizes specifically to a target sequence in the target nucleic acid in a solution phase that contains a denaturant chemical and an immobilized probe that binds specifically to the capture probe, to provide a reaction mixture, incubating the reaction mixture at about 25° C. for about 1 to 60 minutes, thereby forming a hybridization complex made up of the capture probe hybridized specifically to the target nucleic acid and the immobilized probe bound specifically to the capture probe, in which the hybridization complex is attached to a support via the immobilized probe, and separating the hybridization complex attached to the support from other sample components. In a preferred embodiment, the denaturant chemical is urea at a concentration of about 1 M. In other preferred embodiments, the denaturant chemical is imidazole at a concentration between 0.05 M and 0.5 M and incubating is for about 2 to 30 minutes. In a preferred embodiment, imidazole is at a concentration of about 0.5 M and incubating is for about 15 minutes.

A composition for specific capture of a target nucleic acid is disclosed that includes at least one target nucleic acid, at least one capture probe that hybridizes specifically to a target sequence in the target nucleic acid, an immobilized probe that binds specifically to the capture probe, and a solution phase hybridization mixture that contains imidazole at a concentration from 0.05 M to 4.2 M or urea at a concentration from 1 to 8 M. In some preferred embodiments, the mixture contains from 0.05 to 0.5 M imidazole, whereas in other preferred embodiments, the mixture contains from 1.7 M to 3.5 M imidazole. In some preferred embodiments, the hybridization mixture contains from 2.0 M to 2.7 M imidazole. In a preferred embodiment, the composition includes a first capture probe that hybridizes specifically to a first target sequence and a second capture probe that hybridizes specifically to a second target sequence which is different from the first target sequence.

DETAILED DESCRIPTION OF THE INVENTION

Figure 1:
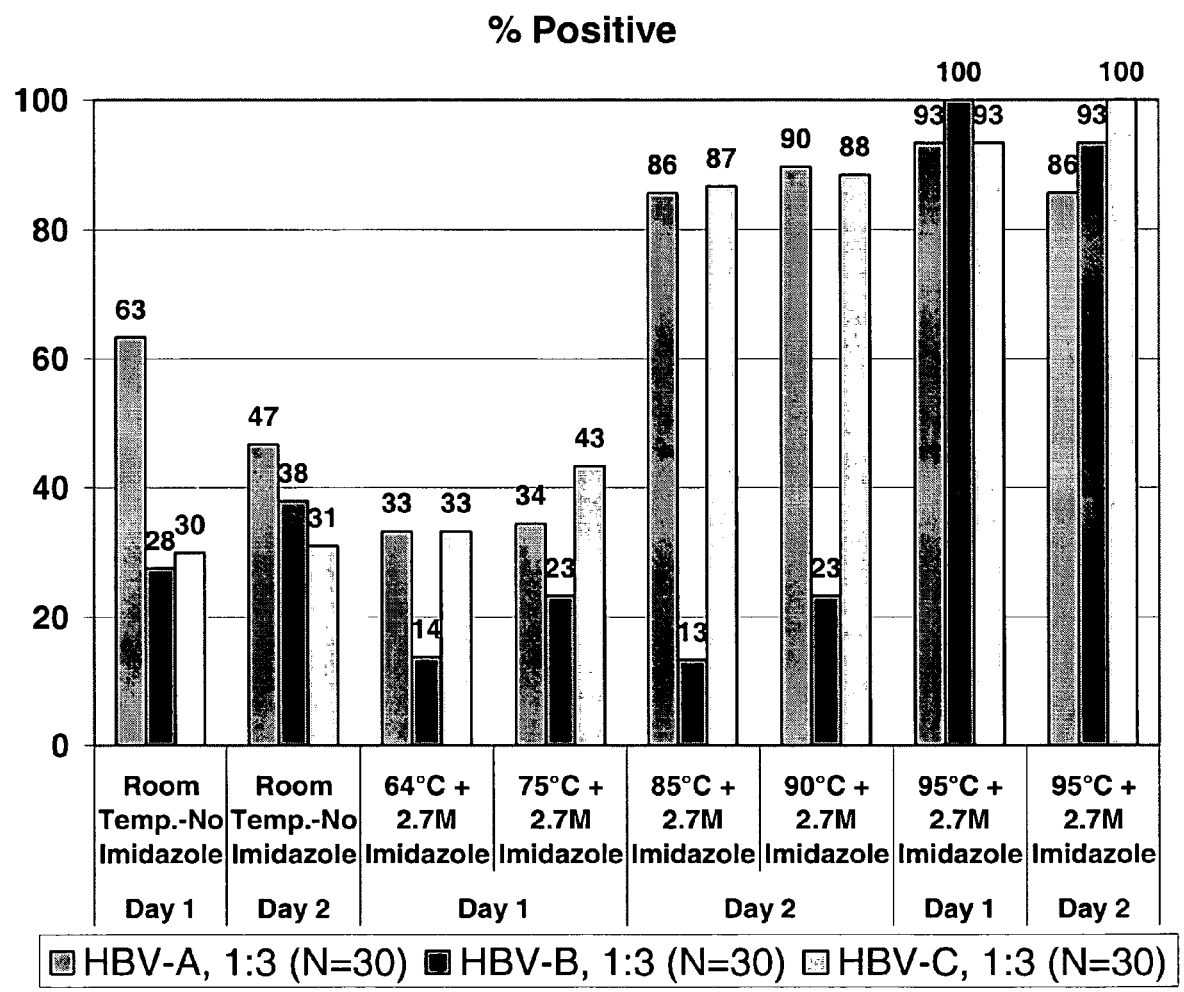
FIG. 1 is a bar graph showing results of target capture in the presence of 2.7 M imidazole in mixtures incubated at room temperature, 64° C., 85° C., and 95° C. for three nucleic acid targets, HBV subtype A (medium shaded bars), HBV subtype B (dark shaded bars), and HBV subtype C (light shaded bars), compared to target capture performed at room temperature in mixtures without imidazole.

The disclosed methods of target capture isolate specific target nucleic acids from a sample by using hybridization of a capture probe to the target nucleic acid in a mixture using hybridization conditions that include a denaturant chemical in a solution, such as imidazole or urea, and incubation of the mixture in a temperature range of about 60° C. to 95° C. for about 2 to 15 minutes. In preferred embodiments, the target nucleic acid is completely or partially double-stranded DNA. Preferred embodiments of the method use hybridization conditions that include 1.7M to 3.2 M imidazole in a solution that contains a capture probe and its target that is incubated at 75° C. to 95° C. for about 3 to 7 minutes.

Another disclosed method isolates a target nucleic acid of interest from a sample in a single incubation step by using specific hybridization of a capture probe to the target nucleic acid and binding of the capture probe to an immobilized probe in a mixture that includes a denaturant chemical in solution, such as 0.5 M imidazole or 1 M urea, incubated at room temperature (about 25° C.) for about 15 to 60 minutes. In preferred embodiments, the capture probe is a nucleic acid oligomer made up of 2'-methoxy RNA groups or includes one or more LNA residues. In a preferred embodiment, 30 minutes of room temperature incubation is used to capture the target nucleic acid of interest using a target-specific capture probe.

These methods are particularly useful for isolating a nucleic acid of interest that is completely or partially double-stranded, or contains other secondary or tertiary structure. Some embodiments use a synergistic effect on hybridization achieved by using a denaturant chemical in solution in a mixture that includes the capture probe and target nucleic acid that is incubated at about 60° C. to 95° C. for a relatively short time, e.g., about 1 to 15 minutes. Preferred embodiments of the target capture method use hybridization conditions in which the denaturant chemical is imidazole at a concentration in a range of about 2.1 M to 4.2 M. Other embodiments use hybridization conditions in which imidazole is in a concentration range of about 2.7 M to 3.2 M. A preferred embodiment of the target capture method uses a hybridization mixture that includes about 2.7 M imidazole in solution and at least one target-specific capture probe specific for at least one target nucleic acid to efficiently bind the target nucleic acid when hybridization conditions include incubation of the mixture for 3 to 7 min at about 75° C. to 95° C., or more preferably at about 85° C. to 95° C.

Target capture methods described herein may be used with two or more capture probes to capture the same target nucleic acid from a sample or to capture two or more different target nucleic acids from the same sample, using one set of target capture conditions. That is, two or more different target-specific capture probes may act in the same reaction mixture and same conditions, each probe specific for its intended target sequence, so long as all the probes exhibit substantially similar hybridization characteristics in the target capture conditions used. For example, one embodiment is a target capture method that uses a first capture probe specific for a first target nucleic acid and a second capture probe specific for a second target nucleic acid that is different from the first target nucleic acid, where the first and second capture probes exhibit substantially similar hybridization characteristics for their respective targets in a single reaction mixture that includes imidazole and is incubated at about 60° C. to 95° C. for a short time before separation of the captured first and second target nucleic acids from other sample components. Another embodiment is a target capture method that uses a first capture probe specific for a first sequence in a target nucleic acid and a second capture probe specific for a second sequence in the same target nucleic acid, where the first and second capture probes exhibit substantially similar hybridization characteristics for their respective target sequences in a single reaction mixture that includes imidazole and is incubated at about 60° C. to 95° C. for a short time before separation of the captured target nucleic acid from other sample components.

Compositions disclosed herein include a target-specific capture probe in a hybridization reaction mixture that includes a denaturant chemical, such as urea or imidazole, to increase efficiency of specific hybridization of the capture probe oligomer to its target sequence, particularly when the target sequence is in a nucleic acid that is partially or fully double stranded, or contains other secondary or tertiary structure. Compositions include components for making a hybridization reaction mixture that includes a denaturant chemical, preferably imidazole, in a solution that may contain one or more target capture reaction components, such as at least one capture probe specific for the intended target nucleic acid, an immobilized binding partner that binds to the capture probe, or chemical components in a hybridization solution (e.g., salts, buffering agents).

These compositions include kits for performing specific polynucleotide target capture that include at least one capture probe specific for an intended target nucleic acid and a denaturant chemical, preferably imidazole, in a solution phase mixture. Preferred kit embodiments contain a solution that contains imidazole, a capture probe oligomer specific for the intended target nucleic acid, and an immobilized binding partner for the capture probe. Other kit embodiments also include one or more components used in treating the isolated captured target nucleic acids in an assay that detects the target nucleic acid in a sample, such as a washing solution for purifying the captured target nucleic acid from other sample components, or components used in in vitro amplification of a sequence contained in the captured target nucleic acid, and/or components used in detection of the captured target nucleic acid or amplification products made from the captured target nucleic acid.

Preferred target capture reagents include at least one capture probe that hybridizes specifically to a sequence in the nucleic acid of interest (i.e., target nucleic acid) and sufficient denaturant chemical to make a hybridization mixture when mixed with a sample containing the target nucleic acid to produce the synergistic effect when the mixture is incubated for a short time at temperatures in a range of about 60° C. to 95° C. Such a mixture may be produced, e.g., by combining a predetermined amount of a target capture reagent containing the capture probe with a sample containing the target nucleic acid. The mixture for achieving these hybridization conditions may be made by mixing the denaturant chemical with the sample containing the target nucleic acid simultaneously with introduction of the capture probe, or the denaturant chemical may be added before or after the capture probe is mixed with the sample. Preferred embodiments use a minimum of addition steps to make the final mixture used in the hybridization conditions for target capture. A preferred target capture reagent includes both the target-specific capture probe and an immobilized binding partner that binds to the capture probe to separated the capture probe-target nucleic acid complex efficiently from other sample components. It will be appreciated that the reagents may include one or more target-specific capture probes, e.g., two or more target-specific capture probes, so long as the probes have substantially the same hybridization characteristics to produce efficient target capture for their respective intended target sequences in the same hybridization conditions that include the denaturant chemical and incubation temperatures chosen. One preferred reagent embodiment includes a first capture probe specific for a first target nucleic acid and a second capture probe specific for a second target nucleic acid that is different from the first target nucleic acid, where the first and second capture probes exhibit substantially similar hybridization kinetics for their respective targets in a single hybridization condition that includes imidazole and incubation of the hybridization mixture from between 25° C. to 95° C. for about 30 minutes or less. Another reagent embodiment includes a first capture probe specific for a first sequence in a target nucleic acid and a second capture probe specific for a second sequence in the same target nucleic acid, where the first and second capture probes exhibit substantially similar hybridization kinetics for their respective target sequences in a single hybridization condition used in target capture.

Compositions and methods described herein are particularly useful for isolation of target nucleic acids that are partially or completely double stranded (e.g., dsDNA) or contain secondary structure (e.g., hairpin structures) under relatively mild conditions. Other known isolation methods often include a step of denaturing the target nucleic acid (e.g., boiling for 5-10 min) to make the target nucleic acid single stranded, but such treatments are difficult to perform, may cause contamination of laboratory personnel or equipment if a container opens or explodes, and may produce structures that make nucleic acid isolation inefficient, e.g., coagulation aggregates or damaged nucleic acids. Moreover, insufficient denaturation or reannealing of the denatured nucleic acids before target capture may result in suboptimal capture.

Methods and compositions described herein are useful for purifying desired nucleic acid sequences from a complex mixture, such as from a sample that contains nucleic acids or cells, which may be treated by using conventional methods to release intracellular nucleic acids into a solution. The methods are useful for preparing nucleic acids for use in molecular biology assays or procedures, such as diagnostic assays that detect a specific sequence, forensic tests that detect the presence of biological material, or tests to detect contaminants in water, environmental or food samples. Methods and compositions described herein are useful for preparing nucleic acids for in vitro nucleic acid amplification which is used in many applications. Because the methods concentrate the target nucleic acids and remove them from other sample components that might interfere with subsequent assay steps, these methods are useful for improving assay specificity and/or sensitivity. The methods are relatively simple to perform, making them useful for screening specimens manually or using automation.

A "sample" or "specimen" refers to any composition in which a target nucleic acid may exist as part of a mixture of components, e.g., in water or environmental samples, food stuffs, materials collected for forensic analysis, or biopsy samples for diagnostic testing. "Biological sample" refers to any tissue or material derived from a living or dead organism which may contain a target nucleic acid, including, e.g., cells, tissues, lysates made from cells or tissues, sputum, peripheral blood, plasma, serum, cervical swab samples, biopsy tissues (e.g., lymph nodes), respiratory tissue or exudates, gastrointestinal tissue, urine, feces, semen, or other fluids or materials. A sample may be treated to physically disrupt tissue and/or cell structure to release intracellular components into a solution which may contain enzymes, buffers, salts, detergents and other compounds, such as are used to prepare a sample for analysis by using standard methods.

"Nucleic acid" refers to a multimeric compound comprising nucleotides or analogs which have nitrogenous heterocyclic bases or base analogs linked together to form a polynucleotide, including conventional RNA, DNA, mixed RNA-DNA, and polymers that are analogs thereof. A nucleic acid "backbone" may be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid may be ribose, deoxyribose, or similar compounds with substitutions, e.g., 2' methoxy or 2' halide substitutions. Nitrogenous bases may be conventional bases (A, G, C, T, U), analogs thereof (e.g., inosine or others; see *The Biochemistry of the Nucleic Acids* 5-36, Adams et al., ed., $11^{th}$ ed., 1992), derivatives of purines or pyrimidines (e.g., $N^4$-methyl deoxygaunosine, deaza- or aza-purines, deaza- or aza-pyrimidines, pyrimidine bases with substituent groups at the 5 or 6 position, purine bases with a substituent at the 2, 6 or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines; U.S. Pat. No. 5,378,825 and PCT No. WO 93/13121). Nucleic acids may include one or more "abasic" residues where the backbone includes no nitrogenous base for one or more positions (U.S. Pat. No. 5,585,481). A nucleic acid may include only conventional RNA or DNA sugars, bases and linkages, or may include both conventional components and substitutions (e.g., conventional bases with 2' methoxy linkages, or polymers containing both conventional bases and analogs). The term includes "locked nucleic acid" (LNA), an analogue containing one or more LNA nucleotide monomers with a bicyclic furanose unit locked in an RNA mimicking sugar conformation, which enhance hybridization affinity for complementary RNA and DNA sequences (Vester et al., 2004, *Biochemistry* 43(42):13233-41). Embodiments of oligomers that may affect stability of a hybridization complex include PNA oligomers, oligomers that include 2'-methoxy or 2'-fluoro substituted RNA, or oligomers that affect the overall charge, charge density, or steric associations of a hybridization complex, including oligomers that contain charged linkages (e.g., phosphorothioates) or neutral groups (e.g., methylphosphonates).

"Oligomer" or "oligonucleotide" refers to a nucleic acid of generally less than 1,000 nucleotides (nt), including those in a size range having a lower limit of about 2 to 5 nt and an upper limit of about 500 to 900 nt. Some preferred embodiments are oligomers in a size range with a lower limit of about 5 to 15 nt and an upper limit of about 50 to 600 nt, and other preferred embodiments are in a size range with a lower limit of about 10 to 20 nt and an upper limit of about 22 to 100 nt. Oligomers may be purified from naturally occurring sources, but preferably are synthesized by using any well known enzymatic or chemical method. Oligomers may be referred to by functional names (e.g., capture probe, primer or promoter primer) which are understood to refer to oligomers.

"Capture probe", "capture oligonucleotide", or "capture oligomer" refers to a nucleic acid oligomer that specifically hybridizes to a target sequence in a target nucleic acid by base pairing and joins to a binding partner on an immobilized probe to capture the target nucleic acid to a support. A preferred embodiment of a capture oligomer includes two binding regions: a target-specific region and an immobilized probe-binding region, usually on the same oligomer, although the two regions may be present on two different oligomers joined together by one or more linkers.

"Immobilized probe", "immobilized oligomer" or "immobilized nucleic acid" refers to a nucleic acid binding partner that joins a capture oligomer to a support, directly or indirectly. An immobilized probe joined to a support facilitates separation of a capture probe bound target from unbound material in a sample. Any support may be used (e.g., matrices or particles in solution), which may be made of any of a variety of materials (e.g., nylon, nitrocellulose, glass, polyacrylate, mixed polymers, polystyrene, silane polypropylene, or metal). Preferred supports are magnetically attractable particles, e.g., monodisperse paramagnetic beads (uniform size ±5%) to which an immobilized probe is joined directly (e.g., via covalent linkage, chelation, or ionic interaction) or indirectly (e.g., via a linker), where the joining is stable during nucleic acid hybridization conditions.

"Separating" or "purifying" refers to removing one or more components of a sample from one or more other sample components, e.g., removing some nucleic acids from a generally aqueous solution that may also contain proteins, carbohydrates, lipids, or other nucleic acids. In preferred embodiments, a separating or purifying step removes the target nucleic acid from at least about 70%, more preferably at least about 90% and, even more preferably, at least about 95% of the other sample components.

"Hybridization conditions" refer to the cumulative physical and chemical conditions under which nucleic acid sequences that are completely or partially complementary form a hybridization duplex or complex, usually by standard base pairing. Such conditions are well known to those skilled in the art, are predictable based on sequence composition of the nucleic acids involved in hybridization complex formation, or may be determined empirically by using routine testing (e.g., Sambrook et al., *Molecular Cloning, A Laboratory Manual*, 2$^{nd}$ ed. (Cold Spring Harbor Laboratory Press, Cold Spring Harbor, N.Y., 1989) at §§ 1.90-1.91, 7.37-7.57, 9.47-9.51, and 11.47-11.57, particularly §§ 9.50-9.51, 11.12-11.13, 11.45-11.47 and 11.55-11.57).

"Sufficiently complementary" means that a contiguous nucleic acid base sequence is capable of hybridizing to another base sequence by standard base pairing (hydrogen bonding) between a series of complementary bases. Complementary sequences may be completely complementary at each position in an oligomer sequence relative to its target sequence by using standard base pairing (e.g., G:C, A:T or A:U pairing) or sequences may contain one or more positions that are not complementary by base pairing (including abasic residues), but such sequences are sufficiently complementary because the entire oligomer sequence is capable of specifically hybridizing with its target sequence in appropriate hybridization conditions. Contiguous bases in an oligomer are at least 80%, preferably at least 90%, and more preferably completely complementary to the intended target sequence.

"Nucleic acid amplification" refers to any well known in vitro procedure that produces multiple copies of a target nucleic acid sequence, or its complementary sequence, or fragments thereof (i.e., an amplified sequence containing less than the complete target nucleic acid). Examples of well known procedures include transcription associated methods, such as transcription-mediated amplification (TMA), nucleic acid sequence-based amplification (NASBA) and others (U.S. Pat. Nos. 5,399,491, 5,554,516, 5,437,990, 5,130,238, 4,868,105, and 5,124,246), replicase-mediated amplification (U.S. Pat. No. 4,786,600), the polymerase chain reaction (PCR) (U.S. Pat. Nos. 4,683,195, 4,683,202, and 4,800,159), ligase chain reaction (LCR) (EP Pat. App. 0320308) and strand-displacement amplification (SDA) (U.S. Pat. No. 5,422,252).

"Detection probe" refers to a nucleic acid oligomer that hybridizes specifically to a target nucleic acid sequence, including an amplified sequence, under conditions that promote hybridization, to allow detection of the target nucleic acid. Detection may either be direct (i.e., a probe hybridized directly to the target) or indirect (i.e., a probe hybridized to an intermediate structure that links the probe to the target). A probe's target sequence generally refers to the specific sequence within a larger sequence which the probe hybridizes specifically. A detection probe may include target-specific sequences and other sequences or structures that contribute to the probe's three-dimensional structure, depending on whether the target sequence is present (U.S. Pat. Nos. 5,118, 801, 5,312,728, 6,835,542, and 6,849,412).

"Label" refers to a moiety or compound that is detected or leads to a detectable signal, which may be joined directly or indirectly to a nucleic acid probe. Embodiments that use direct joining include use of covalent bonds or non-covalent interactions, e.g., hydrogen bonding, hydrophobic or ionic interactions, and chelate or coordination complex formation. Embodiments that use indirect joining include use of a bridging moiety or linker, e.g., via an antibody or additional oligonucleotide(s), which may be used to amplify a detectable signal. Any detectable moiety may be a label, e.g., radionuclide, ligand such as biotin or avidin, enzyme, enzyme substrate, reactive group, chromophore such as a dye or particle (e.g., latex or metal bead) that imparts a detectable color, luminescent compound (e.g. bioluminescent, phosphorescent or chemiluminescent compound), and fluorescent compound. Preferred embodiments include a "homogeneous detectable label" that is detectable in a homogeneous assay system in which, in a mixture, bound labeled probe exhibits a detectable change compared to unbound labeled probe, which allows the label to be detected in a homogeneous fashion without physically removing hybridized from unhybridized labeled probe (U.S. Pat. Nos. 5,283,174, 5,656,207 and 5,658,737). Preferred homogeneous detectable labels include chemiluminescent compounds, more preferably acridinium ester ("AE") compounds, such as standard AE or AE derivatives which are well known (U.S. Pat. Nos. 5,656,207, 5,658,737, and 5,639,604). Methods of synthesizing labels, attaching labels to nucleic acids, and detecting signals from labels are well known (e.g., Sambrook et al., *Molecular Cloning, A Laboratory Manual*, 2nd ed., Chapt. 10, and U.S. Pat. Nos. 5,658,737, 5,656,207, 5,547,842, 5,283,174, and 4,581, 333).

Unless defined otherwise, technical terms used herein have the same meaning as commonly understood by those skilled in the art or in definitions found in technical literature, e.g., *Dictionary of Microbiology and Molecular Biology*, 2nd ed. (Singleton et al., 1994, John Wiley & Sons, New York, N.Y.), *The Harper Collins Dictionary of Biology* (Hale & Marham, 1991, Harper Perennial, New York, N.Y.), and similar publications. Unless described otherwise, techniques employed or contemplated herein are standard well known methods.

The disclosed target capture methods may result from increasing the efficiency of hybridization between a nucleic acid probe and a target nucleic acid in a solution that includes other components. These methods may use a synergistic effect that results when a hybridization mixture containing a denaturant chemical, e.g., imidazole or urea, and is incubated for a short time at elevated temperature, e.g., 60° C. to 95° C. before separation of a hybridization complex that includes the capture probe and target nucleic acid from other mixture components. Preferred embodiments use incubation temperatures of about 75° C. to 95° C. and imidazole in the hybridization mixture to increase the efficiency and rate of specific hybridization between the capture probe and its target sequence. Other preferred embodiments are compositions made up of a solution that contains at least one capture probe oligomer and its intended target nucleic acid in a solution that includes about 1.7 M to 2.7 M imidazole.

Another target capture method, referred to as a "standard" method, uses similar steps but does not include a denaturant chemical in the mixture (U.S. Pat. Nos. 6,110,678, 6,280,952, and 6,534,273). Methods disclosed herein provide efficient target capture under relatively mild conditions, particularly for partially or completely double-stranded target nucleic acids (e.g., dsDNA, dsRNA or DNA/RNA hybrids). The disclosed methods are useful for improving assay performance and sensitivity, particularly for assays that use the isolated target nucleic acids in subsequent procedures, such as in vitro amplification and/or detection. The relatively mild conditions described herein include a denaturant chemical in a hybridization mixture which may be used at room temperature or heated for a short time, e.g., about 60-95° C. for 15 minutes or less.

Preferred capture probe oligomers include a target-specific sequence that binds specifically to a sequence in the target nucleic acid, and a moiety that binds to an immobilized probe for separation of the hybridization complex that includes the target nucleic acid from the rest of the mixture. Some preferred embodiments of capture oligomers include a tail sequence (e.g., a substantially homopolymeric sequence) that hybridizes to a complementary immobilized sequence on a support. Other capture probe embodiments bind to an immobilized probe by using a moiety that is a member of a binding pair (e.g., biotinylated DNA and immobilized avidin or streptavidin). In an embodiment that uses a capture probe with a target-specific sequence and a tail sequence, the capture probe is mixed with a sample that contains the target nucleic acid and, under hybridizing conditions that include the denaturant chemical, the capture probe's target-specific portion hybridizes specifically to its target sequence and the tail portion hybridizes to a complementary immobilized sequence to allow the target sequence linked to the support to be separated from other components. In preferred embodiments, the target-specific portion hybridizes to the target nucleic acid in a first step and the tail portion hybridizes to the immobilized sequence in a second step, which makes use of favorable solution phase hybridization kinetics in the first step. In preferred embodiments, hybridization conditions include a soluble denaturant chemical in the mixture that contains the capture probe and target nucleic acid and incubation of the mixture at 60° C. to 95° C., preferably 75° C. to 95° C., for about 15 min or less to permit formation of a hybridization duplex of the capture probe and target nucleic acid, followed by incubation at a lower temperature (e.g., about 25° C. to 42° C.) to permit formation of a hybridization complex made up of the target nucleic acid, capture oligomer, and immobilized probe. In embodiments in which the capture probe and immobilized probe bind via non-nucleic acid binding pair members, hybridization conditions allow formation of the capture probe-target hybridization duplex and binding of the capture probe and immobilized probe via the binding pair members.

An immobilized probe may be connected to a support by any linkage that is stable in the hybridization conditions used in the target capture method. Preferred embodiments use a support of monodisperse particles which can be retrieved from solution by using known methods, e.g., centrifugation, filtration, magnetic attraction, or other physical or electrochemical separation. The support with the attached hybridization complex that includes the capture probe and target nucleic acid is separated from other sample components. In some embodiments, hybridization complexes bound to the support are washed one or more times under conditions that maintain complexes on the support to further separate other components, including other nucleic acids, from the captured target nucleic acid. The target nucleic acid is isolated and concentrated on the support, i.e., the target nucleic acid concentration on the support that is higher than in the initial sample. The isolated target nucleic acid, attached to or eluted from the support, may be used in a variety of subsequent processes such as in vitro amplification and/or detection.

Target capture methods described herein may be used to isolate two or more target nucleic acids from the same sample simultaneously by including two or more capture probes in the hybridization mixture, each capture probe specific for a target sequence. For example, a hybridization mixture may include a first capture probe specific for a first target and a second capture probe specific for a second target, where each capture probe hybridizes to its intended target under the same hybridization conditions. Each capture probe may bind to the same immobilized probe or may bind to an immobilized probe specific for the individual capture probe. In one embodiment, the first and second capture probes both contain a poly-A tail region and bind to the same immobilized probe that includes a complementary poly-T sequence, thus purifying the first and second targets on the same support. In an embodiment, the first capture probe binds to a first immobilized probe on a first support, and the second capture probe binds to a second immobilized probe on a second support, thus purifying the first target on the first support and the second target on the second support. When the first and second supports exhibit different separation characteristics, the first target on the first support is readily separated from the second target on the second support, even though all of capture complexes formed in the same reaction mixture. These methods may be used to isolate many targets from a single sample by using combinations of different capture probes which all function in substantially the same hybridization conditions to isolate many targets from a mixture.

Initial target capture tests were performed by using samples that contained a known amount of a target RNA (*Chlamydia trachomatis* 23S rRNA) which was hybridized to a labeled detection probe to make a labeled target complex. Target capture was performed on the labeled target complex by using a capture probe that contains a 5' target-specific sequence complementary to a sequence contained in the rRNA and a 3' tail sequence complementary to oligonucleotides immobilized on magnetic beads. Target capture mixtures were incubated under different hybridization conditions, including in solutions with and without a denaturant chemical (urea or imidazole), at room temperature to 60° C., for various times from 1 to 60 min. The captured labeled target complex on the beads was separated from the other mixture components and the target was detected by measuring a signal from the attached labeled probe. Many capture probes specific for different target sequences in the rRNA were tested for target capture efficiency at room temperature and most showed increased capture efficiency when imidazole was included (e.g., 0.05 M to 1 M). Some of the capture probes that were efficient at target capture at room temperature were subsequently tested in different conditions to determine hybridization conditions that increased efficiency and/or kinetics of target capture. For example, some target capture tests also included one or more helper oligonucleotides complementary to a sequence in the rRNA to facilitate binding of another complementary sequence to the target RNA (U.S. Pat. No. 5,030,557). Generally, capture probes were synthesized with 2' methoxy RNA in the target-specific portion and DNA in the tail portion. Relative efficiencies of the target capture conditions were determined by measuring the signal produced from detection probes bound to the captured target after it was separated from the mixture. Different capture probes performed at different efficiencies under the same conditions, but almost all of the tested capture probes showed an increase in target capture efficiency when imidazole was included in the reaction mixture. For example, efficient capture of the rRNA target (75% to 90%) with relatively fast kinetics was observed when target capture mixtures contained 0.5 M imidazole and were incubated at 60° C. for 1 minute, 42° C. for 10 minutes, or room temperature for 15 minutes. These experiments demonstrated that hybridization conditions that included a denaturant chemical generally increased the efficiency and kinetics of target capture compared to similar hybridization conditions that did not include a denaturant chemical in the reaction mixture. Many of these tests showed higher background signals (e.g., in controls that did not contain the target capture probe) when imidazole was present compared to similar assays performed without imidazole, but this was substantially eliminated in later tests by modifying the detection conditions (i.e., increasing the pH of the selection reagent to pH 9.2 and incubating the selection step longer, e.g., 5-10 min). Assays performed with imidazole in the target capture reaction incubated at lower temperatures (25° C. to 42° C.) typically resulted in less total detectable signal compared to target capture assays performed using the same capture probe in a reaction mixture without imidazole incubated at higher temperature (60° C.). An increase in target capture efficiency, however, was repeatedly observed when reaction mixtures contained imidazole compared to matched reactions that did not include imidazole in the mixture, for many different probes and incubation conditions that were tested.

Embodiments of efficient target capture methods were demonstrated in a model system that used a synthetic partially dsDNA target that was captured by using a capture probe that included a target-specific sequence and a tail portion which was complementary to an immobilized oligomer on a particulate support. These components were mixed in a solution containing salts and buffering agents with different concentrations of denaturant chemical and incubated for a short time (10 min or less) at different temperatures (e.g., about 60° C. to 95° C.) for hybridization of the target-specific portion of the capture probe with its target nucleic acid, and then at a lower temperature (e.g., RT to 42° C.) for hybridization of the tail portion to the immobilized oligomer. Particles with the attached complexes were separated from the other components in the mixture and the captured target nucleic acid was detected by detecting a signal from a labeled detection probe hybridized to the target nucleic acid or an amplification product made from the captured target, measured in a homogeneous assay. The model system demonstrated the unexpected result that hybridization between the target-specific region of the capture probe and its target sequence was efficient under relatively mild incubation conditions when a denaturant chemical was included in the hybridization mixture, but the denaturant chemical did not interfere with hybridization between the capture probe tail and the immobilized probe, resulting in an efficient capture of the target. Although not wishing to be bound to a particular theory or mechanism, this may result from increased denaturation of the double-stranded portion of the target DNA, thus making the target sequence accessible to hybridization with the capture probe while not inhibiting other target capture steps.

Viral targets were also used to demonstrate increased target capture efficiency by using the compositions and methods of target capture disclosed herein. One target was BK virus (BKV) which contains a fully dsDNA genome and another target was hepatitis B virus (HBV), which has a partially or fully double-stranded genome depending on its replication phase. When these target viruses were tested using a standard target capture procedure that did not include a denaturant chemical (described in U.S. Pat. Nos. 6,110,678, 6,280,952, and 6,534,273), capture of the viral genomes was suboptimal, e.g, retrieving less than 60% of the target nucleic acid in the sample. Assays for the viruses that used the standard target capture method were relatively insensitive even when the captured viral nucleic acids were amplified in vitro and amplified sequences were detected. Even when the sample containing viral DNA was heated at a high temperature (95° C.) to denature the target DNA before using the standard target capture process, assay sensitivity showed only marginal improvement. In contrast, when embodiments of the efficient target capture method disclosed herein that included imidazole in the target capture reactions were used, the assay sensitivity improved. Embodiments of the efficient target capture process included a combination of including a denaturant chemical, imidazole or urea, in the reaction mixture and heating the mixture at an initial phase in the target capture process, which resulted in a surprising synergistic effect that greatly improved target capture efficiency and assay sensitivity. For example, one embodiment that included imidazole in the target capture process before in vitro nucleic acid amplification resulted in 95% detection rates for HBV in samples that contained HBV subtypes B, C and A (28-fold, 4-fold and 2-fold increased detection rates, respectively, compared to assays that did not include the efficient target capture method). Another embodiment for used urea in the target capture mixture which was incubated at 95° C. during an initial step of the target capture process, after which the captured HBV DNA was amplified in vitro and amplified sequences were detected. Another embodiment for BKV DNA capture included imidazole in the target capture mixture that was incubated for a short time at high temperature followed by a lower temperature, and separation of the captured BKV DNA from other components, which improved the assay sensitivity 10-fold compared to a similar assay that used a standard target capture method. In the comparative assays, the captured BKV DNA was amplified in vitro and amplified BKV sequences were detected by using a labeled detection probe.

Examples are included to describe embodiments of the disclosed target capture methods and compositions. In some cases, after target capture, the captured nucleic acids were subjected to additional steps, e.g., in vitro amplification and/or detection using a labeled probe, by using known methods (e.g., U.S. Pat. Nos. 5,399,491 and 5,554,516, for amplification; U.S. Pat. Nos. 5,283,174, 5,656,207, and 5,658,737, for detection probe labeling, hybridization and detection steps). Some examples describe assays performed with different embodiments of a target capture process that includes a denaturant chemical, which may be compared to assays performed with a standard target capture process that does not include a denaturant chemical (U.S. Pat. Nos. 6,110,678, 6,280,952, and 6,534,273). Unless otherwise specified, reagents commonly used in assays described below are as follows. Sample transport reagent: 110 mM lithium lauryl sulfate (LLS), 15 mM $NaH_2PO_4$, 15 mM $Na_2HPO_4$, 1 mM EDTA, 1 mM EGTA, pH 6.7. Target Capture Reagent (TCR): 789 mM HEPES, 230 mM succinic acid, 10% w/v LLS, 679 mM LiOH, 0.03% anti-foaming agent, pH 6.4, and 100 µg/ml of paramagnetic particles (0.7-1.05µ particles, SERA-MAG™ MG-CM, Seradyne, Inc., Indianapolis, Ind.) with $(dT)_{14}$ oligomers covalently bound thereto, or (C-type) 250 mM HEPES, 1.88 M LiCl, 310 mM LiOH, 100 mM EDTA, pH 6.4, and 250 µg/ml of paramagnetic particles (0.7-1.05µ, particles, Sera-Mag™ MG-CM) with $(dT)_{14}$ oligomers covalently bound thereto. Wash Solution: 10 mM HEPES, 150 mM NaCl, 6.5 mM NaOH, 1 mM EDTA, 0.3% (v/v) ethanol, 0.02% (w/v) methylparaben, 0.01% (w/v) propylparaben, and 0.1% (w/v) sodium lauryl sulfate, pH 7.5. Amplification reagent: a concentrated solution mixed with other TMA reaction components to produce a mixture containing 47.6 mM Na-HEPES, 12.5 mM N-acetyl-L-cysteine, 2.5% TRITON™ X-100, 54.8 mM KCl, 23 mM $MgCl_2$, 3 mM NaOH, 0.35 mM of each dNTP (dATP, dCTP, dGTP, dTTP), 7.06 mM rATP, 1.35 mM rCTP, 1.35 mM UTP, 8.85 mM rGTP, 0.26 mM $Na_2EDTA$, 5% v/v glycerol, 2.9% trehalose, 0.225% ethanol, 0.075% methylparaben, 0.015% propylparaben, and 0.002% Phenol Red, pH 7.5-7.6. Primers and/or probes may be in the amplification reagent or added separately to a mixture. Enzymes for TMA: about 90 U/µl of MMLV reverse transcriptase (RT) and about 20 U/µl of T7 RNA polymerase per reaction (1 U of RT incorporates 1 nmol of dTTP in 10 min at 37° C. using 200-400 µM oligo dT-primed polyA template, and 1 U of T7 RNA polymeras incorporates 1 nmol of ATP into RNA in 1 hr at 37° C. using a T7 promoter in a DNA template). Probe Reagent: AE-labeled detection probes in a solution of (a) 100 mM Li-succinate, 3% (w/v) LLS, 10 mM mercaptoethanesulfonate (MES), and 3% (w/v) polyvinylpyrrolidon, or (b) 100 mM Li-succinate, 0.1% (w/v) LLS, and 10 mM MES. Hybridization Reagent: (C-type) 100 mM succinic acid, 2% (w/v) LLS, 100 mM LiOH, 15 mM aldrithiol-2, 1.2 M LiCl, 20 mM EDTA, and 3.0% (v/v) ethanol, pH 4.7; or (P-type) 190 mM succinic acid, 17% (w/v) LLS, 3 mM EDTA, and 3 mM EGTA, pH 5.1. Selection Reagent: 600 mM boric acid, 182.5 mM NaOH, 1% (v/v) octoxynol (TRITON® X-100), pH 8.5 or pH 9.2, to hydrolyze AE labels on unhybridized detection probe oligomers. Detection Reagents comprise Detect Reagent I: 1 mM nitric acid and 32 mM $H_2O_2$, and Detect Reagent II: 1.5 M NaOH, to produce chemiluminescence from AE labels (see U.S. Pat. Nos. 5,283,174, 5,656,744, and 5,658,737).

For comparison to the target capture methods that include a denaturant chemical, the standard target capture procedure is described briefly. The standard process typically mixes a sample that contains the target nucleic acid (RNA or DNA) with about 1.75 pmols of a capture probe specific for the target nucleic acid (i.e., probe that hybridizes specifically to a sequence contained in the target nucleic acid in the hybridization conditions used) and about 100 µg of immobilized probe attached to paramagnetic particles ($dT_{14}$ probes attached to 0.7-1.05µ particles (Seradyne) by using carbodiimide chemistry (Lund, et al., 1988, *Nuc. Acids Res.* 16:10861-10880)) in target capture reagent. The mixture may include an amplification oligomer (e.g., primer) that hybridizes to the target nucleic acid (U.S. Pat. No.6,534,273). The standard target capture mixture is heated at 55° C. to 60° C. for about 15 to 30 min, then cooled to room temperature (RT) for 5 to 15 min, to allow sequential hybridization of the capture probe and target nucleic acid and then the immobilized probe to the capture probe:target nucleic acid complex. A magnetic field is applied to separate particles with attached complexes from the solution phase and concentrate them in the container (U.S. Pat. No.4,895,650) and the supernatant is removed. Particles are washed by suspending them in Wash Solution (e.g., 1 ml at RT) and repeating the magnetic separation.

Captured target nucleic acids may be detected by using a detection process or may be treated by in vitro nucleic acid amplification to amplify part of the target nucleic acid sequence which is detected. For example, for transcription mediated amplification (TMA), washed particles are suspended in 75 µl of amplification reagent with primers and enzymes added to make a mixture that is incubated at 41.5-42° C. for 1-2 hr (U.S. Pat. Nos. 5,399,491 and 5,554,516). Amplified sequences may be detected by using an AE-labeled probe that hybridizes specifically to an amplified sequence and chemiluminescence from the AE label on bound probes is detected, expressed as relative light units (RLU) (U.S. Pat. No. 5,658,737, see column 25, lines 27-46, Nelson et al., 1996, *Biochem.* 35:8429-8438 at 8432), although any of a variety of in vitro amplification methods and/or detection methods may be used.

Target capture methods described herein include a denaturant chemical, preferably imidazole, in a solution phase mixture that includes a capture probe specific for the intended target nucleic acid, reagents for making a mixture for promoting nucleic acid hybridization (e.g., salts, buffering agents), a target nucleic acid (generally added from a sample), and an added immobilized probe, preferably in a suspension. A target capture mixture may include additional oligomers used in an assay, e.g., helper oligomers, in vitro amplification primer oligomers, and/or detection probe oligomers. In some embodiments, the denaturant chemical is in target capture reagents that include the capture probe which are mixed with the sample containing the target nucleic acid to make a mixture that is incubated at an elevated temperature (e.g., 60° C. to 95° C.) for a brief time (e.g., 1 to 15 min). In a preferred embodiment, the mixture is incubated at 75° C. to 95° C. for about 3 min, and then the target capture process is performed. Although specific temperatures and incubation times used in particular embodiments of the efficient target capture method may vary based on the chosen combination of a particular capture probe and target nucleic acid, the method includes a denaturant chemical in the target capture mixture which is incubated for a short time (e.g., 1 to 30 min, preferably 1 to 15 min) at hybridization temperature (e.g., room temperature to 95° C.) before the separation step that removes the captured target from the mixture. In addition to increasing assay sensitivity, the target capture methods described herein are easy to perform, manually or in an automated system, and add only a few minutes to the total assay time. Embodiments of the efficient target capture method disclosed herein are useful for improving assay sensitivity for target nucleic acids that are partially or completely double-stranded, or contain regions of secondary or tertiary structure.

EXAMPLE 1

Target Capture of RNA Known to Have Secondary and Tertiary Structure

This example demonstrates that hybridization conditions that include imidazole generally increased efficiency and kinetics of target capture of a RNA known to have secondary and tertiary structure (23S rRNA) at relatively low incubation temperatures, e.g., RT to about 42° C. for many capture probes. Secondary and/or tertiary structure in the target RNA may inhibit interaction with a capture probe and limit target capture. Experiments were performed by using a known amount of *Chlamydia trachomatis* 23S rRNA which was hybridized to a labeled detection probe complementary to a sequence in the rRNA to label the target RNA before it was captured. Typically, 200 fmole of 23S rRNA was hybridized with 1 pmole of an AE-labeled synthetic oligonucleotide in hybridization reagent (60° C. for 30 min, followed by cooling to RT). An aliquot of the hybridized detection probe:target mixture was mixed with target capture reagent (TCR) containing a capture probe, immobilized probe, with or without a known concentration of denaturant chemical, and mixture was incubated at RT (about 25° C.) to 60° C. for 1 to 60 min before collection of the captured target. The capture probes (SEQ ID Nos. 6 to 30) each contained a 5' target-specific sequence complementary to a sequence contained in the rRNA and a 3' $A_{30}$ tail sequence, synthesized with 2' methoxy RNA in the target-specific region and a DNA tail region. Immobilized probes were $dT_{15}$ oligonucleotides attached to magnetic microparticles as supports (SERA-MAG™). Some assays included in the target capture reaction mixture one or more helper oligonucleotides complementary to a separate sequence in the rRNA to facilitate binding of another complementary sequence to the target rRNA (U.S. Pat. No. 5,030,557, Hogan et al.). Denaturant chemicals were 1 M urea or 0.05 M to 1.8 M imidazole. Following target capture, the labeled rRNA targets attached to magnetic particles were separated from the solution phase by using magnetic attraction, the supernatant was removed, particles with attached complexes were washed multiple times with a wash solution, and chemiluminescence from the labeled probe bound to the target, following hydrolysis of AE labels in unhybridized detection probes using selection reagent, was detected in a luminometer (as relative light units (RLU), substantially as described in U.S. Pat. No. 5,658,737).

Target capture assays performed at RT or 60° C. in the presence of 1M urea increased the detected RLU from the captured RNA (2.2 to 3.1-fold higher) compared to signals detected from matched samples that were treated identically except that no urea was in the target capture mixture. Because aqueous solutions of urea may decompose on heating (giving off $NH_3$), additional experiments were performed using imidazole in target capture mixtures.

In a series of assays, capture probes (SEQ ID Nos. 6 to 29) specific for different target sequences in the 23S rRNA were tested individually for target capture efficiency at RT in the presence of imidazole (0.05-1 M) and all except one showed increased target capture when imidazole was present compared to a matched reactions in which the mixtures did not contain imidazole (e.g., 1.3-fold to 8.8-fold increase in RLU detected in the immobilized portion). Some of the capture probes (SEQ ID Nos. 6, 8, 17, 20-22, 24 and 27) were tested subsequently by using different hybridization conditions (incubated at 25° C., 42° C. and 60° C., with and without imidazole present). Relative efficiencies of target capture were determined for each capture probe and condition by measuring the chemiluminescence produced from detection probes bound to the captured target separated from the solution phase. The different capture probes tested individually at RT in reactions that contained no imidazole captured the rRNA at different efficiencies (0% to 70% of initial target), whereas all of the capture probes except one captured more rRNA when 0.5 M imidazole was present in the reaction (2.6% to 89% of inital target). For example, one capture probe demonstrated high levels of rRNA capture when reactions containing 0.5M imidazole were incubated at RT (about 75% of target captured by 15 min), or 42° C. (about 90% of target captured by 10 min), or 60° C. (about 90% of target captured at 1 min). In contrast, in the absence of imidazole, at RT, target capture was inefficient (11% of the target was captured by 60 min).

To measure the kinetics of target capture, capture probes (SEQ ID Nos. 6, 20, 21 and 24) were used at RT in hybridization mixtures that contained no imidazole or 0.05 to 0.1 M imidazole to capture C. trachomatis 23S rRNA. The probes showed more target capture after 5 min incubation in reactions that contained 0.1 M imidazole compared to matched reactions without imidazole. Capture probes (SEQ ID Nos. 6, 20, 21) were tested in similar assays incubated at RT for 2, 15, and 30 minutes. Increased target capture was seen for all of the probes in the presence of 0.05 M imidazole after only 2 min incubation compared to matched reactions without imidazole. One capture probe (SEQ ID NO:20) was tested subsequently in reactions that contained no or 0.05 M imidazole, incubated at RT, 42° C., or 60° C., for 5, 15, or 30 min before measuring signal from the captured target. Target capture efficiency increased for all conditions that included imidazole in the mixtures compared to the matched reactions without imidazole, with the greatest increases seen after 5 min (2.2-fold increase at RT, 1.7-fold increases at 42° C. and 60° C.) compared to longer incubations (1.7-fold increase at RT, 1.3-fold increases at 42° C. and 60° C. for 15 min; 1.4-fold increase at RT, 1.1 to 1.2-fold increases at 42° C. and 60° C. for 30 min). The results demonstrate increased kinetics of target capture in the presence of imidazole.

EXAMPLE 2

Target Capture of a Synthetic Target Present in a Partially Double-Stranded DNA

This example demonstrates efficiencies of target capture when the reaction mixtures contained different concentrations of imidazole, all incubated at 60° C. for 15 min, followed by incubation at RT for 30 min. For these tests, a partially double-stranded DNA (dsDNA) was made by synthesizing a strand of SEQ ID NO:1 and its complementary strand (SEQ ID NO:2), hybridizing the two strands together (35 pmol of each in 20 μl of hybridization reagent (P-type), incubated at 60° C. for 1 hr, and cooled to RT). The resultant dsDNA contained, at one end, a 30 nt single-stranded DNA that is complementary to a detection probe (SEQ ID NO:4). Each target capture reaction mixture contained 10 fmoles of dsDNA target in 0.2 ml of sample transport reagent to which was added 0.2 ml of target capture reagent (TCR, C-type) containing 0 to 3.18 M imidazole, 0.1 ml of TCR containing 50 μg of paramagnetic particles (Sera-Mag™) with covalently attached $dT_{14}$ oligomers, and 20 pmoles of a capture probe (SEQ ID NO:3) that contains a 5' target-specific region (25 nt of LNA complementary to a sequence in the target strand of the dsDNA) and a 3' polyA tail region. Reactions were incubated at 60° C. for 15 min, then at RT for 30 min, and the captured target DNA attached to the magnetic supports was separated from the supernatant as described above. The pellet was washed once (using 0.5 ml of hybridization reagent, P-type), and then AE labeled detection probe (100 fmoles of SEQ ID NO:4 in 0.1 ml of hybridization reagent, P-type) was mixed with the pellet and the mixture was incubated at 60° C. for 15 min to hybridize the probe to the captured strand. Chemiluminescence from the bound detection probes was detected substantially as described above (0.2 ml of selection reagent, pH 9.2, added to each mixture, incubated at 60° C. for 7 min, and Detect Reagents I and II added sequentially to produce chemiluminescence detected in a luminometer for 5 sec). A background control that contained no target was treated similarly. Results of these tests are shown in Table 1, reported as net RLU (background RLU subtracted from each total detected RLU) and the percentage of initial target that was captured for each reaction. The results show that the presence of 2.38 M and 3.18 M imidazole in the reaction mixtures greatly increased the target capture from the sample compared to reactions that included lesser amounts or no imidazole in the same conditions.

TABLE 1

Capture of a Target Strand from dsDNA at Different Imidizole Concentrations

| Imidazole (M) | Detected Captured Target (RLU) | Captured Target (%) |
|---|---|---|
| 0 | 442 | 0.6 |
| 0.24 | 446 | 0.6 |
| 0.48 | 574 | 0.76 |
| 0.96 | 607 | 0.81 |
| 1.43 | 1010 | 1.34 |
| 1.91 | 2342 | 3.1 |
| 2.38 | 17621 | 24 |
| 3.18 | 50109 | 67 |

Additional tests were performed using the same conditions except that the target capture mixtures contained 0 to 3.4 M imidazole. Results are shown in Table 2, which show that about a third or more of the initial target was captured from reactions incubated at 60° C. that contained 2.6 M to 3.4 M imidazole, and 65% or more of the target was captured from mixtures that contained 3 M to 3.4 M imidazole.

TABLE 2

Capture of a Target Strand from dsDNA

| Imidazole Conc. (M) | Net RLU Detected | % Target Captured |
|---|---|---|
| 0 | 688 | 0.92 |
| 1.5 | 1957 | 2.6 |
| 2.0 | 5283 | 7.0 |
| 2.2 | 10856 | 14.5 |
| 2.4 | 15812 | 21.0 |
| 2.6 | 24366 | 32.5 |
| 2.8 | 36872 | 49.2 |
| 3.0 | 51127 | 68.2 |
| 3.2 | 56916 | 76.0 |
| 3.4 | 48971 | 65.2 |

EXAMPLE 3

Target Capture of a Target Strand Present in Synthetic dsDNA

Additional tests were performed using conditions substantially as described in Example 2, but using different synthetic versions of the capture probe that contained LNA or DNA residues in the 5' target-specific region (nt 1-25 of SEQ ID NO:3). Each target capture reaction included 20 fmoles of the dsDNA target in 0.2 ml of sample transport reagent to which was added 0.2 ml of TCR (C-type) containing from 0 to 4.2 M imidazole, 0.1 ml of TCR containing 50 µg of magnetic particles (Sera-Mag™) with covalently attached dT$_{14}$ oligomers, and 20 pmoles of capture probe that contained LNA or DNA residues in the 5' target-specific sequence. Reactions were incubated at 60° C. for 15 min, then at RT for 30 min, and treated as described above for capture, washing, and detection steps. Controls were treated similarly but contained no target (background control) or contained no capture probe (net RLU: 92). Results of these tests are shown in Table 3, reported as net RLU (background RLU subtracted from total detected RLU) and the percentage of target captured for each reaction condition. The results show that 3.5 M and 4.2 M imidazole present in the reaction mixtures increased target capture efficiency compared to reactions that contained 2.1 M imidazole. Increased target capture efficiency was seen for both the LNA and DNA capture probes, with more target captured with the LNA probe compared to the DNA probe.

TABLE 3

Capture of a Target Strand from dsDNA Using LNA and DNA Probes

| Capture Probe | Imidazole Conc. (M) | Detected Net RLU | % Target Captured |
|---|---|---|---|
| DNA | 2.1 | 6781 | 4.4 |
| | 3.5 | 92189 | 61 |
| | 4.2 | 33378 | 22 |
| LNA | 2.1 | 8101 | 5.4 |
| | 3.5 | 100277 | 66.4 |
| | 4.2 | 43007 | 28.5 |

Additional target capture assays were performed by using substantially the same conditions described above, but using 3.2 M imidazole in the reaction mixtures and capture probes that contained different LNA portions were compared to a DNA capture probes of the same sequence. In those tests, a capture probe that was completely or partially LNA in the 25-nt target-specific region was more efficient for target capture than the DNA capture probe (64-65% compared to 57.4% for the DNA probe). A capture probe that was LNA in the target-specific region and part of the tail region (10 of 30-nt polyA) further increased target capture efficiency (86%) compared to the DNA probe (57.4%).

Using substantially the same target capture conditions with or without 3.2 M imidazole in the reactions, two different detection probes specific for the target strand (SEQ ID NO:1) were used to determine whether the partially dsDNA target (SEQ ID NO:1 hybridized to SEQ ID NO:2) was denatured during the target capture procedure. One detection probe (SEQ ID NO:4, AE labeled at nt 18-19) was specific for a target sequence at the 5' end of the target strand, i.e., the portion of the partially dsDNA that is single-stranded under all conditions. The second detection probe (SEQ ID NO:5, AE labeled at nt 18-19) was specific for a target sequence at the 3' end of the target strand, i.e., in the portion of the partially dsDNA that is double-stranded when added to the target capture mixture. The target capture reaction mixtures containing either the LNA (nt 1-25) capture probe or the DNA capture probe were incubated at 60° C. for 20 min, then at RT for 20 min, and treated as described above for magnetic capture, washing, and detection steps using separate aliquots for the two detection probes. For comparison, a DNA strand of SEQ ID NO:1 was detected with each detection probe to determine the signal for a completely single-stranded target. Without imidazole in the target capture reactions, capture of the target strand from the partially dsDNA target was relatively inefficient (3.8-9.2%), whereas with imidazole in the target capture reactions, capture of the target strand was efficient (79-100%). When imidazole was in the target capture reactions, the detection signals from both of the detection probes were similar, i.e., for a target capture mixture following capture, RLU detected using the 3' detection probe was similar to the RLU detected using the 5' detection probe. These results show that captured strand was single stranded from mixtures that included imidazole and were incubated at 60° C.

EXAMPLE 4

Target Capture of HBV Subtype B With Imidazole and 95° C. Incubation

This example shows that imidazole present in the target capture reagent (TCR) improved sensitivity of HBV subtype B detection in an assay format that combines target capture, in vitro amplification of HBV sequences (TMA), and detection of the amplified sequence by using chemiluminescent labeled probes (U.S. Pat. No. 5,790,219, McDonough et al., US Publ. No. 20040029111, Linnen et al.; PROCLEIX® Ultrio Hepatitis B Virus (HBV) Discriminatory Assay (dHBV), Chiron Corp., Emoryville, Calif.). This example shows that imidazole present during target capture, in conjunction with a high temperature incubation, significantly improved assay sensitivity. These conditions were tested using samples from a clinical serum panel known to contain HBV subtype B (used at a 1:3 dilution). Twenty replicates were tested for each experimental condition to determine the effect of the target capture modifications against control assay conditions that used the standard target capture process followed by the same amplification and detection assay steps. Negative controls (7 replicates) contained normal serum (no HBV) and were treated identically. Assays were conducted using the supplier's instructions (PROCLEIX® Ultrio Hepatitis B Virus (HBV) Discriminatory Assay (dHBV) package insert IN0142 Rev. 1 and 10-01-07-271 Rev. C.1), summarized as follows. Imidazole (crystalline, FW 68.08) was added directly into standard target capture reagent (TCR) to a final concentration of 1.7 M or 2.7 M. Control sample tubes contained 500 µl of sample and 400 µl of TCR without imidazole. In the modified target capture method, tubes received an additional 400 µl of TCR containing imidazole to a final concentration of 1.7 M or 2.7 M in 800 µl of TCR. Target capture tubes that did not receive a 95° incubation step were sealed, mixed, held at RT for 15 min, incubated at 60° C. for 20 min, and then at RT for 15 min before separation of the hybridization complexes on the magnetic supports. Target capture tubes that received a 95° C. incubation step were sealed, mixed, incubated at 95° C. for 15 min without agitation, then incubated at 60° C. for 20 min, and RT for 15 min. Tubes were treated to separate magnetically the particles with captured nucleic acids, wash the captured nucleic acids on the particles, and then handled to perform the in vitro amplification and detection of HBV sequences. Briefly, captured HBV nucleic acids were amplified for specific sequences by using a combination of HBV specific primers and TMA to produce amplified products that were detected by hybridization with labeled probes that bind specifically to the amplified HBV sequences (US Publ. No. 20040029111). Signals from the labels associated with bound probes were produced and detected as chemiluminescence (RLU) in a homogeneous detection assay. Results shown in Table 4.

TABLE 4

HBV Detection Using Different Target Capture Conditions

| Sample (No. Tested) | Initial Heating Step | TCR ± Imidazole | % Positive | Mean RLU |
|---|---|---|---|---|
| Negative control (n = 7) | none | 400 µl TCR | 0 | 748 |
| HBV-B Panel (n = 20) | none | 400 µl TCR | 30 | 830,181 |
| HBV-B Panel (n = 20) | none | 800 µl TCR + 1.7 M imidazole | 50 | 803,816 |
| HBV-B Panel (n = 20) | none | 800 µl TCR + 2.7 M imidazole | 25 | 852,630 |
| Negative control (n = 7) | 95° C. for 15 min | 400 µl TCR | 0 | 1,080 |
| HBV-B Panel (n = 20) | 95° C. for 15 min | 400 µl TCR | 44 | 1,078,457 |
| HBV-B Panel (n = 20) | 95° C. for 15 min | 800 µl TCR + 1.7 M imidazole | 100 | 971,403 |
| HBV-B Panel (n = 20) | 95° C. for 15 min | 800 µl TCR + 2.7 M imidazole | 100 | 1,046,232 |

The results show that the target capture process that included imidazole in the reactions and a 95° C. incubation improved detection of HBV in the assays compared to assays that used a target capture procedure that did not include imidazole in the reaction mixture and 95° C. incubation.

EXAMPLE 5

Efficient Target Capture of HBV Subtypes A, B and C Over a Range of Temperatures This example shows that the efficient target capture method described in Example 4 improved assay sensitivity for HBV subtypes A and C, and the improved target capture efficiency associated with the presence of imidazole occurs over a temperature range. The target capture procedures conducted with use of imidazole at various temperatures were tested using samples of HBV clinical serum panels for subtypes A, B and C. Thirty replicates of each subtype (at 1:3 dilution) were tested to determine the effect on target capture of TCR containing 2.7 M imidazole incubated for 12 min at 64° C., 75° C., 85° C., 90° C. or 95° C. Assays were performed substantially as described in Example 4, but at different temperatures. Some of the results of the tests are shown in FIG. 1, including those for a control in which TCR contained no imidazole and incubation was at RT ("Room Temp.—No Imidazole"). The results show the effect of the presence of 2.7 M imidazole during target capture using three incubation temperatures (64° C., 85° C., and 95° C.) for three different HBV nucleic acid targets: subtype A (medium shaded), subtype B (dark shaded), and subtype C (light shaded). The percentage of positive results (y-axis) are shown for samples tested using the different conditions (x-axis), for assays performed on separate days (Day 1 and Day 2). Numbers above the bars indicate the percent positive detection of HBV for the tested samples. From these and other results, the efficient target capture method that included imidazole was shown to improve assay sensitivity over a broad temperature range for HBV subtypes A and C (from about 75° C. to 95° C.), but over a narrower temperature range for HBV subtype B (from about 90° C. to 95° C.).

EXAMPLE 6

Target Capture of a Partial dsDNA/RNA Virus, HBV Subtype B

This example shows that the efficient target capture method that combines imidazole in the reaction mixture and 95° C.

incubation can be performed for a shorter time than typically required for nucleic acid denaturation at high temperature. That is, the synergistic effect achieved by using 2.7 M imidazole and 95° C. incubation was demonstrated in a short time range.

Figure 2:
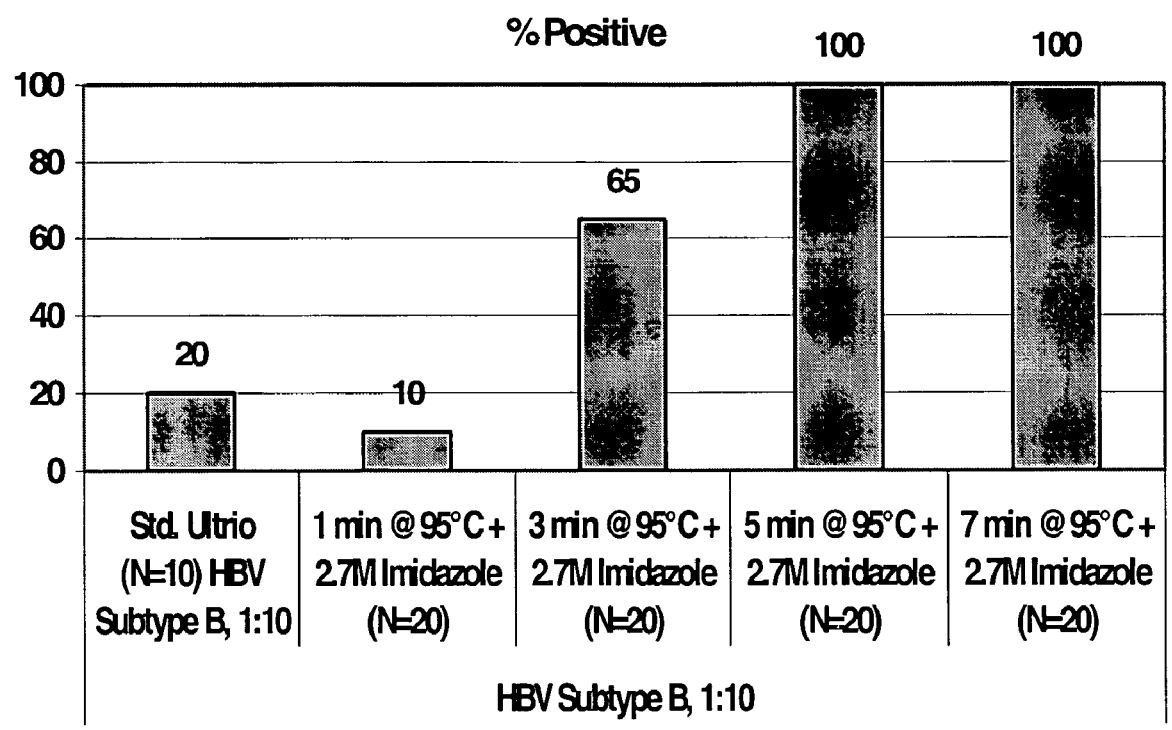
FIG. 2 is a bar graph showing results of target capture of HBV subtype B nucleic acid from mixtures containing 2.7 M imidazole incubated for 1, 3, 5, and 7 min at 95° C. compared to results of target capture performed in mixtures without imidazole.

Assays were performed substantially as described in Examples 4 and 5, but using different incubation times. The target capture process that includes imidazole in TCR was tested on samples of a HBV subtype B clinical serum panel. Twenty replicates (at 1:10 dilution) were tested using TCR containing 2.7 M imidazole in mixtures incubated at 95° C. for 1, 3, 5 and 7 min. The TCR also contained an internal control nucleic acid unrelated to the target nucleic acid. The tests were compared to similar tests performed by using the standard target capture process. For both sets of tests, captured nucleic acids were used in amplification and detection steps performed substantially as described in Examples 4 and 5. Results shown in FIG. 2 demonstrate that a 95° C. incubation step of as short at 3 min when imidazole is present in the target capture mixture improved assay sensitivity significantly compared to the same assay performed by using the standard target capture method that does not include imidazole in the mixture or a 95° C. incubation. FIG. 2 shows the increase in percent positive detection (y-axis and number over each bar) for the conditions tested (x-axis). The results show that incubation for 3 min or more at 95° C. is adequate to produce the synergistic effect that increases target capture efficiency in the presence of imidazole, which results in increased assay sensitivity.

EXAMPLE 7

Target Capture Performed with Different Chemical Denaturants

This example demonstrates the effects on detection of a DNA target when a target capture process includes target capture in the presence of 8 M urea or 2 M Imidazole and incubation at 95° C. The target polynucleotide was a sequence specific to HBV genotype C. Twenty replicate samples were tested for each condition in assays performed substantially as described Examples 5 and 6, i.e., different target capture processes followed by identical in vitro amplification of the captured nucleic acids and detection of amplified sequences. These assays compared results obtained when samples were subjected to target capture with the following variables: (1) TCR plus 8 M urea, (2) 95° C. incubation, (3) TCR plus 8 M urea plus 95° C. incubation, and (4) TCR plus 2 M imidazole plus 95° C. incubation, all compared to a standard target capture process that does not include urea or imidazole in reactions or 95° C. incubation. Briefly, the assay protocol was as follows. Three TCR versions were made and then used immediately thereafter: TCR with 2 M imidazole, TCR with 8 M urea, and standard TCR (no urea or imidazole). Each reaction tube contained 400 µl of one TCR version, into which was added 500 µl of HBV genotype C (HBV-C) or 500 µl of normal serum (negative controls). Tubes were sealed and mixed. Some tubes were incubated at 95° C. for 10 min, followed by RT for 5 min, whereas other tubes remained at RT for 15 min (i.e., no 95° C. incubation). Then, the standard target capture protocol was followed as described above (60° C. for 20 min, RT for 15 min, magnetic separation of particles with captured nucleic acids, and wash step). Captured target polynucleotides were amplified by using TMA with primers specific for HBV and amplified sequences were detected by using AE-labeled probes specific for the amplified sequence to produce chemiluminescence which was detected (RLU) and used to determine whether the assays produced positive or negative results (RLU greater than 50,000 were considered positive). Results of the assays are summarized in Table 5.

TABLE 5

HBV Type C Detection in Assays Using Different Target Capture Conditions

| Samples | TCR | 95° C. Incubation | % Positive Results |
| --- | --- | --- | --- |
| HBV-C | Standard | No | 35% |
| HBV-C | +2.0 M imidazole | Yes | 100% |
| HBV-C | +8.0 M urea | Yes | 100% |
| HBV-C | +8.0 M urea | No | 25% |
| HBV-C | Standard | Yes | 25% |
| Negative Controls | Standard | No | 0% |

The results show that the presence 2 M imidazole or 8 M urea in the target capture reaction mixture combined with 95° C. incubation greatly increased sensitivity of the assay to detect the HBV target. Target capture conditions that included a denaturant chemical (imidazole or urea) in the reaction mixtures incubated at 95° C. demonstrated the synergistic effect of these conditions, compared to target capture mixtures that used only the 95° C. incubation or that included urea but without the 95° C. incubation.

We claim:

1. A method for isolating a target nucleic acid of interest from a sample, comprising:

mixing a sample containing a target nucleic acid with a capture probe that hybridizes specifically to a target sequence in the target nucleic acid in a detergent-containing solution phase that contains imidazole in a concentration range of 0.5 M to about 4.2 M and an immobilized probe that binds specifically to the capture probe, to provide a reaction mixture, incubating the reaction mixture at a first temperature in a range of about 85° C. to 95° C. for about 15 minutes or less, incubating the reaction mixture at a second temperature in a range of about 25° C. to 42° C. for about 20 minutes or less, thereby forming a hybridization complex made up of the capture probe hybridized specifically to the target nucleic acid and the immobilized probe bound specifically to the capture probe, wherein the hybridization complex is attached to a support via the immobilized probe, and separating the hybridization complex attached to the support from other sample components.

2. The method of claim 1, wherein the solution phase contains imidazole at a concentration from 0.5 M to 4.2 M, and incubating at the first temperature is for about 1 to 15 minutes.

3. The method of claim 1, wherein the solution phase contains imidazole at a concentration from 3.0 M to 3.5 M, and incubating at the first temperature is for about 1 to 15 minutes.

4. The method of claim 1, wherein the solution phase contains imidazole at a concentration from 2.0 M to 2.7 M and incubating at the first temperature is about 90° C. to 95° C. for about 3 to 10 minutes.

5. The method of claim 1, wherein the solution phase contains imidazole at 2.7 M, incubating at the first temperature is for about 3 to 15 minutes, and the method further includes incubating the reaction mixture at about 60° C. for about 20 minutes between the first and second incubating steps.

6. The method of claim 1, wherein incubating at the first temperature is about 95° C. for about 3 to 15 minutes.

7. The method of claim 1, wherein the target nucleic acid is completely or partially double-stranded nucleic acid, or a nucleic acid that includes other secondary or tertiary structure.

8. The method of claim 1, wherein the capture probe is made up of a target-specific sequence that binds to the target nucleic acid and a tail region that binds to the immobilized probe via a specific binding partner.

9. The method of claim 8, wherein the tail region binds to the immobilized probe by hybridizing specifically to a complementary sequence of the immobilized probe.

10. The method of claim 1, further comprising after the separating step, a step of detecting the target nucleic acid or an in vitro amplification product made from the target nucleic acid.

11. A method for isolating a target nucleic acid of interest from a sample, comprising:
mixing a sample containing a target RNA with a nucleic acid capture probe that contains a first sequence that hybridizes specifically to a target sequence in the target RNA in a solution phase that contains a detergent and imidazole in a concentration range of 1.7 M to 2.7 M and an immobilized probe that binds specifically to the capture probe, to provide a reaction mixture,
first incubating the reaction mixture at 85° C. to 95° C. for 3 to 15 minutes,
second incubating the reaction mixture at about 25° C. to 42° C. for about 5 to 15 minutes, thereby forming a hybridization complex made up of the capture probe hybridized specifically to the target RNA and the immobilized probe hybridized specifically to the capture probe, wherein the hybridization complex is attached to a support via the immobilized probe, and
separating the hybridization complex attached to the support from other sample components, thereby isolating the target RNA from other sample components.

12. The method of claim 11, wherein the second incubating step is at about 25° C. for about 5 minutes.

13. The method of claim 11, wherein the method further includes incubating the reaction mixture at 60° C. for about 20 minutes between the first and the second incubating step which is at about 25° C. for about 15 minutes.

14. The method of claim 1, wherein the solution phase contains imidazole at a concentration from 1.7 M to 3.2 M and the incubating step at the first temperature is for about 3 to 7 minutes.

15. The method of claim 1, wherein the mixing step includes a first capture probe that hybridizes specifically to a first target sequence and a second capture probe that hybridizes specifically to a second target sequence which is different from the first target sequence and wherein the incubating and separating steps are performed by using one set of target capture conditions.

16. A method for isolating a target nucleic acid of interest from a sample, comprising:
mixing a sample containing the target nucleic acid with a nucleic acid capture probe that contains a first sequence that hybridizes specifically to a target sequence in the target nucleic acid in a detergent-containing solution phase that contains about 1.7 M to 2.7 M imidazole and an immobilized probe that binds specifically to the capture probe, to provide a reaction mixture,
incubating the reaction mixture at a first temperature of about 85° C. to 95° C. for about 10 to 15 minutes,
then incubating the reaction mixture at a second temperature of about 60° C. for about 20 minutes,
then incubating the reaction mixture at a third temperature of about 25° C. for about 5 to 15 minutes, thereby forming a hybridization complex made up of the capture probe hybridized specifically to the target nucleic acid and the immobilized probe hybridized specifically to the capture probe, wherein the hybridization complex is attached to a support via the immobilized probe, and
separating the hybridization complex attached to the support from other sample components, thereby isolating the target nucleic acid from other sample components.

17. The method of claim 16, wherein the solution phase contains imidazole at a concentration of about 1.7 M.

18. The method of claim 16, wherein the solution phase contains imidazole at a concentration of about 2.0 M.

19. The method of claim 16, wherein the solution phase contains imidazole at a concentration of about 2.7 M.

20. The method of claim 16, wherein the mixing step includes a first capture probe that hybridizes specifically to a first target sequence in a first target nucleic acid and a second capture probe that hybridizes specifically to a second target sequence in a second target nucleic acid, thereby permitting formation of two different hybridization complexes under the same incubation conditions, and permitting separation of two different hybridization complexes attached to the support from other sample components, thereby isolating the first target nucleic acid and the second target nucleic acid from other sample components.

* * * * *